United States Patent [19]

DeRemigis

[11] 4,097,153
[45] Jun. 27, 1978

[54] METHOD AND APPARATUS FOR MEASURING THE ELECTROPHORETIC MOBILITY OF SUSPENDED PARTICLES

[75] Inventor: Joseph DeRemigis, New Market, Canada

[73] Assignee: Sentrol Systems Ltd., Downsview, Canada

[21] Appl. No.: 686,835

[22] Filed: May 17, 1976

[51] Int. Cl.² .................. G01N 21/00; G01P 3/36; B01K 5/00; G01B 9/02
[52] U.S. Cl. .................................... 356/103; 356/28; 356/105; 356/106 R; 250/574; 204/180 R
[58] Field of Search ............... 356/105, 102, 103, 107, 356/28, 106 R; 250/564, 565, 574, 575; 204/180 R

[56] References Cited

U.S. PATENT DOCUMENTS

| 3,539,262 | 11/1970 | Pryor | 356/107 |
| 3,553,462 | 1/1971 | Johnson | 250/565 |
| 3,649,125 | 3/1972 | Lehmann | 356/104 |
| 3,708,402 | 1/1973 | Bean | 356/105 |
| 3,732,014 | 5/1973 | Uzgiris | 356/103 |
| 3,740,553 | 6/1973 | Whetten | 250/574 |
| 3,866,055 | 2/1975 | Pike | 250/564 |
| 3,875,516 | 4/1975 | Thomas | 250/564 |

Primary Examiner—Samuel W. Engle
Assistant Examiner—Donald P. Walsh
Attorney, Agent, or Firm—Shenier & O'Connor

[57] ABSTRACT

Coherent electromagnetic radiation is directed upon particles suspended in a fluid medium to produce scattered radiation. The particles are subjected to an electric field alternating between a first and second intensity. The coherent radiation and the scattered radiation are directed upon a detector to produce a heterodyne signal the spectrum of which is analyzed. The spectral composition of the heterodyne signal obtained with the first intensity of applied electric field is compared with the spectral composition obtained with the second intensity of applied electric field to provide a measurement of the electrophoretic mobility of the suspended particles.

25 Claims, 4 Drawing Figures

METHOD AND APPARATUS FOR MEASURING THE ELECTROPHORETIC MOBILITY OF SUSPENDED PARTICLES

BACKGROUND OF THE INVENTION

This invention relates to a method and apparatus for measuring the electrophoretic mobility of particles suspended in a fluid medium and, in particular, to a method and and apparatus using a laser Doppler velocimeter (LDV).

Often it is desirable to obtain accurate measurements of the velocity of suspended particles undergoing electrophoretic motion. From such measurements, for example, the electrokinetic or Zeta potential may be readily calculated using the Helmholtz-Smoluchowski equation $u = ZKE/4\pi h$ where $u$ is the velocity of the suspended particles, Z is the Zeta potential of the suspended particles, K is the dielectric constant of the suspending medium, E is the intensity of the applied electric field, and $h$ is the viscosity of the fluid medium. While there exist mechanical methods for measuring the velocity of particles undergoing electrophoretic motion, these methods necessarily disturb the motion of the particles and thus are capable of only a limited degree of precision.

An alternative method of measuring the velocity of suspended particles is to measure the Doppler shift in frequency of an incident light beam. Generally, this method consists of directing electromagnetic radiation of a fixed frequency upon the particles, collecting a frequency-shifted reflected beam from the particle, and comparing the shifted frequency with the original frequency to obtain a measurement of the particle velocity. The frequency comparison is usually performed by mixing or heterodyning samples of the original and reflected signals to obtain a heterodyne signal, the frequency of which is equal to the difference between the frequencies being compared. Since the difference frequency is proportional to both the velocity of the moving object and the frequency of the incident signal, accurate measurement of the velocity of slowly moving suspended particles in fluid media necessitates using extremely high frequency coherent signals such as are provided by lasers. A typical Doppler velocimeter employing a laser light source is shown in U.S. Pat. No. 3,732,014, issued to E. Uzgiris.

One of the problems associated with this velocimeter and other velocimeters of the prior art used to measure the speed of slowly moving particles arises from the fact that the incident laser beam is scattered not only by the particles under study, but also by the fluid medium in which the particles are suspended. Since the molecules forming the fluid medium are themselves undergoing constant thermal motion having some component at all velocities, the scattering caused by the medium will contribute to the heterodyne signal a "noise" signal having a component at all frequencies including the characteristic frequency of the particles under study. As a result, the heterodyne signal component contributed by the particles under study may be partially or totally obscured by the noise signal contributed by the medium.

SUMMARY OF THE INVENTION

One of the objects of my invention is to provide a method and apparatus for measuring the electrophoretic mobility of particles suspended in a fluid medium.

Another object of my invention is to provide a method and apparatus for measuring the electrophoretic mobility of particles suspended in a fluid medium using a laser Doppler velocimeter.

A further object of my invention is to provide a method and apparatus for measuring the electrophoretic mobility of particles suspended in a fluid medium which is relatively insensitive to scattering caused by the suspending medium.

Still another object of my invention is to provide a method and apparatus for measuring the electrophoretic mobility of particles suspended in a fluid medium which can discriminate between electrophoretic motion and motion due to macrosopic flow of the suspending medium.

Other and further objects will be apparent from the following description.

In general, my invention contemplates a method and apparatus for measuring the electrophoretic mobility of solid particles suspended in a fluid medium in which a coherent beam of electromagnetic radiation is directed upon the particles to produce a scattered beam while, simultaneously, the particles are subjected to an electric field alternating between a first and second intensity. The coherent beam and the scattered beam are directed upon a detector to produce a heterodyne signal the spectrum of which is analyzed. The spectral composition of the heterodyne signal obtained with the first intensity of applied electric field is compared with the spectral composition obtained with the second intensity of applied electric field to provide a measurement of the electrophoretic mobility of the suspended particles.

BRIEF DESCRIPTION OF THE DRAWINGS

In the accompanying drawings which form part of the instant specification and which are to be read in conjunction therewith and in which like reference numerals are used to indicate like parts in the various views.

DESCRIPTION OF THE PREFERRED EMBODIMENT

Figure 1:
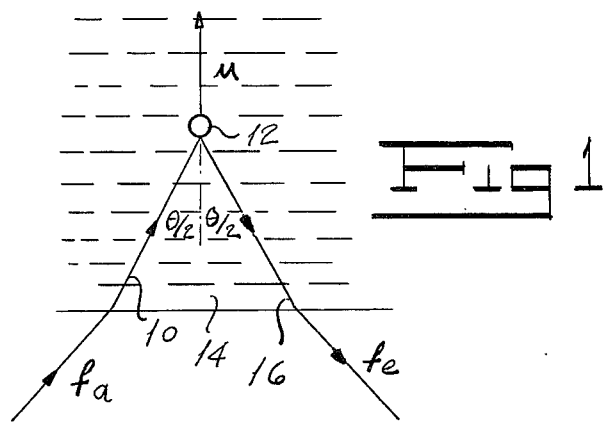
FIG. 1 is a diagrammatic view illustrating the physical principles involved.

The principle of velocity measurement using a Doppler velocimeter, described above in general terms, is illustrated in the case of a moving suspended particle in FIG. 1. In FIG. 1, an incident beam of radiation 10 having a frequency $f_a$ is directed upon a particle 12 suspended in a medium 14 to produce a scattered beam 16 having a frequency $f_e$ at a scattering angle of $\theta$. If the particle is moving at a speed that is small compared with the speed of light, the scattered beam 16 will be Doppler shifted by a frequency $f_s = 2u(n/c)f_a\cos(\theta/2)$, where $n$ is the index of refraction of the medium 14, $c$ is the speed of light in a vacuum, and $u$ is the component of the particle velocity along a line bisecting the scattering angle $\theta$.

Figure 2:
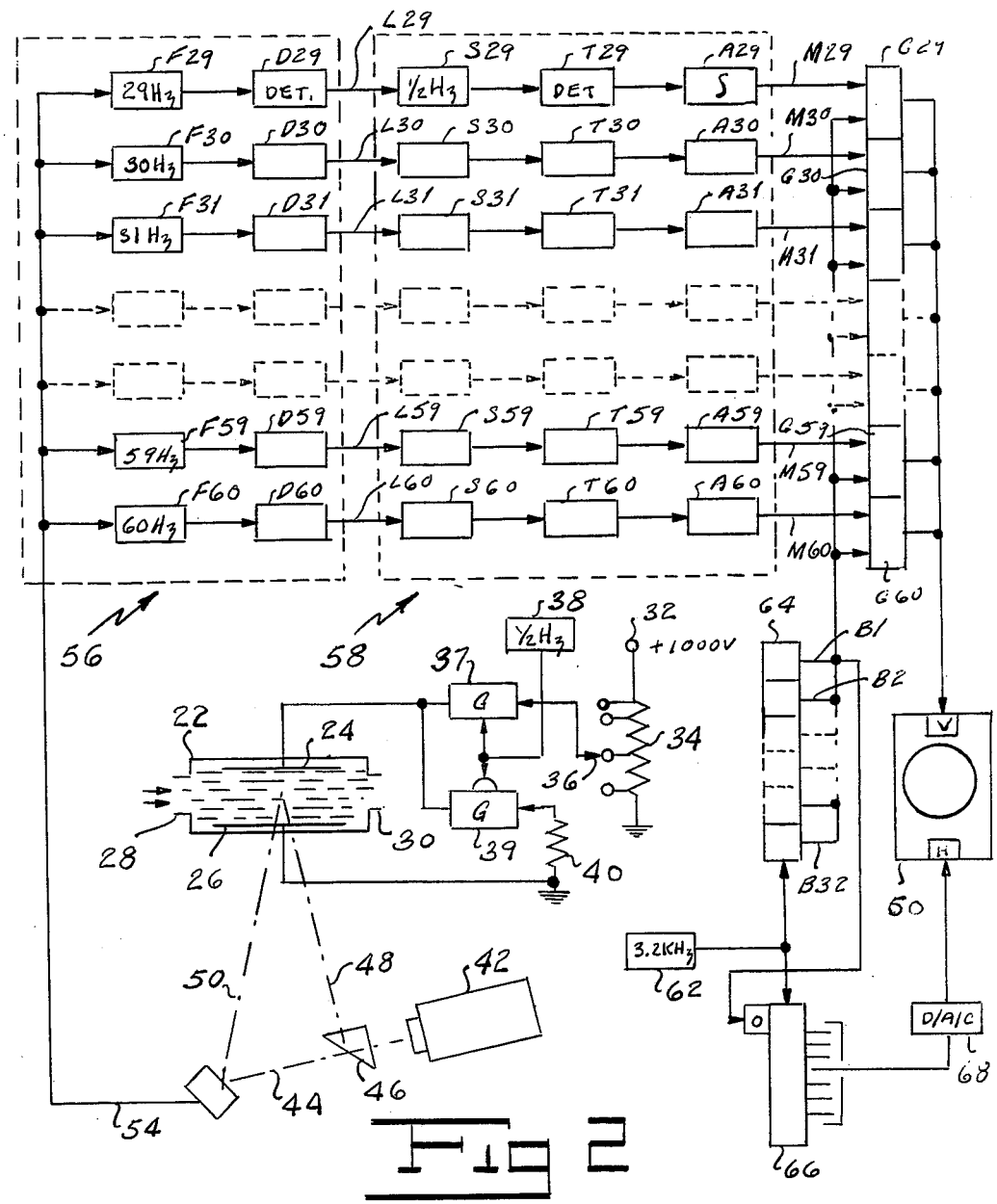
FIG. 2 is a schematic view illustrating a first embodiment of my invention.

Referring now to FIG. 2, my apparatus includes a sample cell 22 having a pair of spaced parallel electrodes 24 and 25 and respective inlet and outlet orifices 28 and 30 through which a sample suspension is pumped. To provide a suitable pulsed potential difference to the electrodes 24 and 26, a DC potential source 32 of 1000 volts, for example, is coupled to one terminal of a tapped resistor 34, the other terminal of which is grounded. Preferably the taps of resistor 34 are located so as to provide a regular progression of voltages such as 250 volts, 350 volts, 500 volts, 700 volts, and 1000 volts. The tapped outputs of the resistor 34 are connected to the fixed contacts of a five-position selector switch 36, the armature of which is coupled to the input of a first gate 37. (It is to be understood that the term "gate", as used herein, refers to a circuit whose output is equal to the input when enabled and is uncoupled from both the input and ground when the gate is inhibited.) Gate 37 has an enabling input which is driven by a 0.5 Hz square wave oscillator having an "on" time and an "off" time of one second each. Oscillator 38 also drives an inhibiting input of a second gate 39, the input of which is grounded through a resistor 40. The outputs of gates 37 and 39 are both coupled to the sample cell electrode 24. The other electrode 26 is grounded. It will be seen that this circuit applies between the electrodes 24 and 26 a pulsed potential difference which is alternately zero and some nonzero value.

A continuous wave laser 42 supplies a reference beam 44 of coherent radiation which is directed upon a beam splitter 46 to obtain an incident beam 48. Beam 48 is in turn directed into the sample cell 22 to obtain a scattered beam 50 which has been scattered by the particles under study. Both the scattered beam 50 and the reference beam 44 are directed upon a suitable square-law or other nonlinear detector 52 such as a photomultiplier tube to produce a heterodyne signal on line 54 whose frequency components correspond to the difference between the respective frequency components of the reference beam 44 and the scattered beam 50.

Since the particle motion of interest is that normal to the parallel surfaces of electrodes 24 and 26, it is preferably that the incident beam 48 and the scattered beam 50 be so directed that the angle formed by these beams is bisected by a perpendicular to said surfaces. It is also desirable that the scattering angle be relatively small, since the magnitude of the Doppler shift is proportional to the cosine of half the scattering angle. In the system shown, good results have been obtained using a scattering angle of approximately 15°. It is necessary, of course, that both the electrode 26 and the adjacent sample cell wall be constructed of suitable transparent materials to permit unobstructed transmission of the beams 48 and 50.

The composite heterodyne signal on line 54 comprises a narrow-band signal generated by the electrophoretic motion of the particles under study, superimposed upon a "noise" signal generated by the random thermal motion of the molecules of the fluid medium. The narrow-band signal, which is modulated by the 0.5 Hz signal generated by the square wave oscillator 38, will lie in the frequency range between 29 Hz and 60 Hz for a suitable level of applied pulsed voltage. To analyze the spectrum of the heterodyne signal within the range, it is applied to a spectrum analyzer circuit indicated generally by the reference numeral 56. The spectrum analyzer 56 includes thirty-two contiguous bandpass filters F29, F30, . . . , F59, and F60, tuned respectively to the frequencies of 29 Hz, 30 Hz, . . . , 59 Hz, and 60 Hz, each of which has a double-sided or total bandwidth of 1 Hz and has its input coupled to line 54. Preferably, the filters F29 through F60 have a constant output over their pass band, although this is not essential to their operation. Each of the filters F29 through F60 is in turn coupled to one of a corresponding plurality of detectors D29 through D60, which may be any suitable type such as a rectifier or squarer.

The outputs of the detectors D29 through D60, which are carried on respective lines L29 through L60, provide indications of the intensity of the heterodyne signal in each of the 1 Hz bands between 29 Hz and 60 Hz. These outputs will fluctuate randomly, at a maximum frequency of approximately 0.5 Hz, about a positive value corresponding to the mean spectral content in that 1 Hz frequency band. In addition, the detectors coupled to those filters tuned near the frequency of the narrow-band signal will produce signals having a periodic component corresponding to the 0.5 Hz envelope of the narrow-band signal. To separate this periodic component, the outputs of the detectors D29 through D60 are fed to a comparer circuit indicated generally by the reference characters 58. The comparer 58 includes a plurality of identical band-pass filters S29 through S60 driven respectively from lines L29 through L60 and having a center frequency of 0.5 Hz corresponding to the switching frequency of the potential applied to electrode 24. The bandwidth of filters L29 through L60 should be sufficiently narrow to discriminate between the periodic component and the randomly fluctuating component of the signals on lines L29 through L60, but should not be so narrow that the filter output cannot attain a reasonable value within a given sampling period. If, for example, the sampling period is 30 seconds, a suitable doublesided bandwidth would be on the order of 0.016 Hz. Each of the outputs of filters S29 through S60 is fed to a corresponding one of a plurality of detectors T29 through T60 which, like the detectors D29 through D60, may be of any suitable type such as a squarer or a rectifier. Finally, each of the detector outputs T29 through T60 is fed to a corresponding one of a plurality of smoothing, integrating, or averaging circuits A29 through A60 having a time constant comparable to the sampling period. In the embodiment shown in FIG. 2, the averagers comprise integrators which integrate or average the detector outputs over a period of 30 seconds.

The outputs of the averagers A29 through A60, which represent the heterodyne signal component in each 1 Hz band due to the electrophoretic motion of the particles, appear on respective lines M29 through M60 which are used to drive the vertical deflection input of a cathode ray oscilloscope 60. To provide proper timing, a 3200 Hz oscillator 62 is coupled to an indexing input of a 32-stage ring counter 64. Counter outputs B1 through B32 are applied to the respective enabling inputs of a plurality of gates G29 through G60. Lines M29 to M60 are coupled through gates G29 to G60 respectively to the vertical deflection input of oscilloscope 60.

To provide a suitably timed horizontal sweep input to the oscilloscope 60, the 3200 Hz oscillator 62 is also coupled to an indexing input of a five-bit binary counter 66. The counter outputs are coupled to a digital-to-analog converter 68. The 100 Hz sawtooth sweep output of converter 68 drives the horizontal deflection input of oscilloscope 60. The B1 output of ring counter 64 resets the output of binary counter 66 to zero.

The operation of my system is best understood by comparison with systems of the prior art. If the applied electric field were simply held at a constant value, each of the detector outputs L29 through L60 would fluctuate randomly about a long term average corresponding to the magnitude of the heterodyne signal produced both by the thermal motion of the suspending medium and by electrophoretic motion of the suspended particles. Even if the detector outputs were averaged over an arbitrarily long time interval, they would still yield a spectral density curve having a broad-band background component centered around 0 Hz, corresponding to the thermal motion of the medium, and a narrow-band "signal" component, centered around a nonzero frequency, corresponding to the electrophoretic motion of the particles. Since the magnitude of the background component is large compared with that of the "signal" component, precisely locating the narrow-band peak will be difficult or impossible.

In the system shown and described, each of the signals on lines L29 through L60 additionally comprises a 0.5 Hz periodic component corresponding to the difference or change in magnitudes of the heterodyne signal with and without voltage applied between electrodes, and hence with and without electrophoretic motion. By measuring this periodic component alone over a sufficiently long period of time, a spectral density curve can be constructed which represents only the signal generated by the particles under study and effectively discriminates against the background components that are present independently of applied potential.

Thus, with no applied field, the nominal output on a given line of the spectrum analyzer due to background thermal motion of fluid molecules is N. With a field applied, the nominal output on such line will be $\sqrt{N^{21}+S^2}$, where S is the signal caused by electrophoretic motion of suspended particles. It can be shown that for large ratios of N to S, the output on a given line of the comparison circuit will be $S^2/2N$. For example, if $N/S=10$ in a given 1 Hz frequency band within the region from 28.5 Hz to 60.5 Hz, then the comparator output for such 1 Hz frequency band will be $S/20$. It will be seen then that while my conduit discriminates against background "noise" of fluid molecules, there is a corresponding decrease in the detected amplitude of the signal due to electrophoretic motion of suspended particles.

Figure 3:
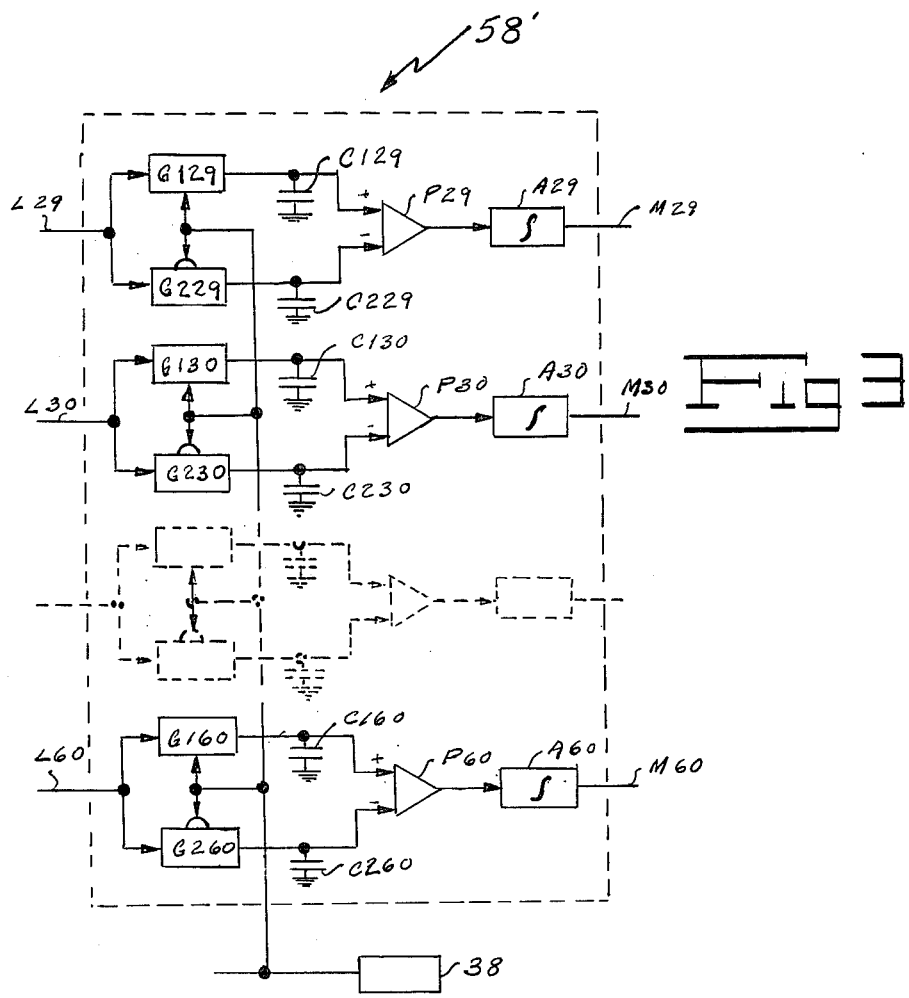
FIG. 3 is a fragmentary schematic view illustrating a second embodiment of my invention.

FIG. 3 shows an alternative comparer circuit 58' which operates synchronously with the switching oscilator 38. In the comparer circuit 58', the signal on line L29 is coupled through a first gate G129 to the positive input of a differential amplifier P29 and through a second gate G229 to the negative input of amplifier P29. Similarly, lines L30 through L60 are coupled through first gates G130 through G160 and second gates G230 through G260 to the respective positive and negative input of amplifiers P30 through P60. The output of oscillator 38 enables the first gates G129 through G160 and disables or inhibits the second gates G229 through G260. Each of the gate outputs is coupled to ground through a capacitor (such as C129 and C229) which in effect "holds" a gate output during any half cycle in which the gate is inhibited. This not only ensures that the differential amplifiers P29 through P60 operate linearly, since the magnitudes of the amplifier inputs are more nearly equal over the entire switching cycle, but also minimizes any spurious output which might otherwise result from an asymmetric switching signal from the oscillator 39, having unequal "on" and "off" times. The outputs of amplifiers P29 through P60 are coupled to the low-pass filters or integrators A29 through A60 in FIG. 2.

Figure 2A:
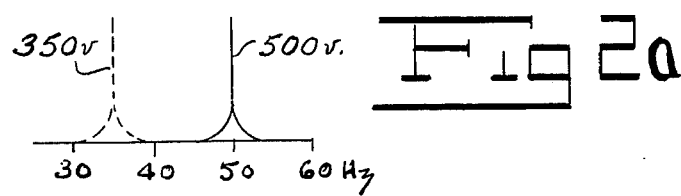
FIG. 2a is a graph showing oscilloscope displays obtained with my invention.

Referring now to FIG. 2a, there is shown in solid lines a graph of the presentation on an oscilloscope 60 for an applied potential of 500 volts, assuming the suspended particles produce a beat or heterodyne frequency of 50 Hz. It will be noted that there is a sharply defined peak at 50 Hz and that the relatively larger background components due to thermal motion of the suspending fluid molecules are entirely suppressed. If the armature of switch 36 is actuated to change the applied potential to 350 volts, the oscilloscope display will be as shown by the dotted line in FIG. 2a and will comprise a sharply defined peak at 35 Hz.

It will be seen that I have accomplished the objects of my invention. I have provided a method of and apparatus for measuring the electrophoretic mobility of particles suspended in a fluid medium which is insensitive to and discriminates against background noise caused by the fluid medium itself. In my invention, the voltage between the plates of the sampling cell is modulated at a low frequency rate by periodically switching the applied field intensity between zero and some predetermined finite value.

It will be understood that certain features and subcombinations are of utility and will be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what I claim is:

1. In an apparatus for measuring the electrophoretic mobility of particles suspended in a fluid medium including a source of coherent electromagnetic radiation, means for directing source radiation upon said suspended particles to produce scattered radiation dependent in frequency on the velocity of said particles in a certain direction, a radiation detector, means for coupling source radiation and scattered radiation to said detector, said detector providing a heterodyne signal, and analyzer means for determining the spectral composition of said heterodyne signal, the improvement comprising means for applying to the suspended particles respective first and second electric fields in said direction over first and second measuring intervals, the magnitudes of said applied fields in said direction being constant over the duration of said measuring intervals, and comparison means for determining changes in the spectral composition of said heterodyne signal between said first and second measuring intervals.

2. The improvement as in claim 1 in which said radiation detector comprises a photomultiplier tube.

3. The improvement as in claim 1 in which said radiation source comprises a laser.

4. The improvement as in claim 1 in which said analyzer means comprises a plurality of band-pass filters, a corresponding plurality of detectors, and means for coupling each filter to a corresponding detector.

5. The improvement as in claim 1 in which one of said electric field magnitudes is zero.

6. The improvement as in claim 1 in which the analyzer means includes a band-pass filter having a certain bandwidth and in which the electric fields alternate at a frequency which is not appreciably greater than half said bandwidth.

7. The improvement as in claim 1 in which said electric fields alternate at a certain frequency and in which the comparison means comprises a band-pass filter tuned to said frequency.

8. The improvement as in claim 1 in which said electric field means includes a pair of parallel spaced electrodes, means for maintaining one electrode at a reference potential, and means for applying to the other electrode a voltage which alternates between said reference potential and a second potential.

9. The improvement as in claim 8 wherein said electric field means includes means for adjusting said second potential to one of a plurality of discrete voltages each different from said reference potential.

10. The improvement as in claim 1 in which said electric field means includes a pair of parallel spaced electrodes and wherein source radiation is directed substantially perpendicular to said electrodes.

11. The improvement as in claim 1 in which the comparison means includes a plurality of band-pass filters each tuned to the same frequency.

12. The improvement as in claim 1 in which the comparison means includes a differential amplifier having a first and a second input, means coupling the analyzer means to the first input synchronously with application of said first field, and means coupling the analyzer means to the second input synchronously with application of said second field.

13. The improvement as in claim 12 further including a first storage capacitor coupled to the first input and a second storage capacitor coupled to the second input.

14. In an apparatus for measuring the electrophoretic mobility of particles suspended in a fluid medium including a source of coherent electromagnetic radiation, means for directing source radiation upon said suspended particles to produce scattered radiation dependent in frequency on the velocity of said particles in a certain direction, a radiation detector, means for coupling source radiation and scattered radiation to said detector, said detector providing a heterodyne signal, and means for determining the spectral composition of said heterodyne signal, the improvement comprising means for applying to the suspended particles respective first and second electric fields in said direction over first and second measuring intervals, the magnitudes of said applied fields in said direction being constant over the duration of said measuring intervals, said first field producing a first spectral composition of the heterodyne signal and said second field producing a second spectral composition of the heterodyne signal, and means for comparing the first and second spectral compositions.

15. In a method for measuring the electrophoretic mobility of particles suspended in a fluid medium including the steps of producing coherent electromagnetic radiation, directing said coherent radiation onto said suspended particles to produce scattered radiation dependent in frequency on the velocity of said particles in a certain direction, directing said scattered radiation and said coherent radiation onto a radiation detector to produce a heterodyne signal, and determining the spectral composition of said heterodyne signal, the improvement comprising the steps of applying to the suspended particles over a first measuring interval a first electric field to provide a first spectral composition of the heterodyne signal, applying to the suspended particles over a second measuring interval a second electric field to provide a second spectral composition of the heterodyne signal, the magnitudes of said applied fields in said direction being constant over the duration of said measuring intervals, and comparing the first and second spectral compositions to determine differences therebetween.

16. In an apparatus for measuring the electrophoretic mobility of particles suspended in a fluid medium including a source of coherent electromagnetic radiation, means for directing radiation from said source upon said suspended particles to produce scattered radiation dependent in frequency on the velocity of said particles in a certain direction, a radiation detector, and means for directing said scattered radiation and radiation from said source not scattered by said particles onto said detector to produce a heterodyne signal, the improvement comprising means for applying to said medium an electric field in the form of spaced pulses, the magnitude of said electric field in said direction being constant over the duration of said pulses and being substantially zero between said pulses, and means for comparing the heterodyne signal produced during said pulses with the signal produced between said pulses to determine the effect of said field on the motion of said particles.

17. In an apparatus for measuring the electrophoretic mobility of particles suspended in a fluid medium including a source of coherent electromagnetic radiation, means for directing radiation from said source upon said suspended particles to produce scattered radiation dependent in frequency on the velocity of said particles in a certain direction, a radiation detector, and means for directing said scattered radiation and radiation from said source not scattered by said particles onto said detector to produce a heterodyne signal, the improvement comprising means for applying to said medium over respective first and second measuring intervals first and second electric fields, the magnitudes of said applied fields in said direction being constant over the duration of said measuring intervals, and means for comparing the heterodyne signal produced during the application of said first electric field with the heterodyne signal produced during the application of said second electric field.

18. In a method for measuring the electrophoretic mobility of particles suspended in a fluid medium including the steps of directing coherent radiation from a source onto said suspended particles to produce scattered radiation dependent in frequency on the velocity of said particles in a certain direction, and directing said scattered radiation and radiation from said source not scattered by said particles onto a radiation detector to produce a heterodyne signal, the improvement comprising applying to said medium over respective first and second measuring intervals first and second electric fields, the magnitudes of said applied fields in said direction being constant over the duration of said measuring intervals, and comparing the heterodyne signal produced during the application of said first electric field with the heterodyne signal produced during the application of said second electric field.

19. The improvement as in claim 16 in which said comparing means comprises means responsive to said detector for providing a signal, means for sampling said signal during said pulses to produce a first output, means for sampling said signal between said pulses to produce a second output, and means for subtractively combining said first and second outputs.

20. The improvement as in claim 19 in which said subtractive combining means subtracts said second signal from said first signal.

21. The improvement as in claim 16 in which said comparing means is equally but oppositely responsive to the heterodyne signal produced during said pulses and to the signal produced between said pulses.

22. The improvement as in claim 17 in which said first and second measuring intervals occur periodically in alternating sequence.

23. The improvement as in claim 17 in which said comparing means comprises means responsive to said detector for providing a signal, means for sampling said signal during said first measuring interval to produce a first output, means for sampling said signal during said second measuring interval to produce a second output, and means for subtractively combining said first and second outputs.

24. The improvement as in claim 23 in which said first and second measuring intervals occur periodically in alternating sequence.

25. The improvement as in claim 17 in which said comparing means is equally but oppositely responsive to the heterodyne signal produced during said first measuring interval and to the signal produced during said second measuring interval.

* * * * *